（12）United States Patent
Hastings et al.

(10) Patent No.: US 8,742,775 B2
(45) Date of Patent: Jun. 3, 2014

(54) ZINC OXIDE SULFUR SENSOR

(75) Inventors: Jedidiah M. Hastings, Kansas City, MO (US); Yong Tian, Peoria, IL (US); Xiaodong Liu, Peoria, IL (US); Douglas A. Rebinsky, Peoria, IL (US); Orhan Altin, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 423 days.

(21) Appl. No.: 12/817,936

(22) Filed: Jun. 17, 2010

(65) Prior Publication Data

US 2011/0012625 A1  Jan. 20, 2011

Related U.S. Application Data

(60) Provisional application No. 61/226,401, filed on Jul. 17, 2009.

(51) Int. Cl.
*G01R 27/08*  (2006.01)

(52) U.S. Cl.
USPC ........ 324/693; 204/422; 204/426; 205/786.5; 73/61.41

(58) Field of Classification Search
USPC ........ 205/781, 786.5; 204/422, 417; 73/61.41
See application file for complete search history.

(56) References Cited

U.S. PATENT DOCUMENTS

| | | | |
|---|---|---|---|
| 3,853,474 A | 12/1974 | Austin | |
| 4,406,754 A | 9/1983 | Narita et al. | |
| 4,409,336 A | 10/1983 | Oita | |
| 5,342,490 A | 8/1994 | Lever et al. | |
| 6,200,445 B1 * | 3/2001 | Yokota et al. | 204/424 |
| 6,623,620 B2 * | 9/2003 | Lai et al. | 205/786.5 |
| 6,716,336 B2 | 4/2004 | Hurland et al. | |
| 6,749,754 B1 | 6/2004 | Holder et al. | |
| 6,914,279 B2 * | 7/2005 | Lu et al. | 506/39 |
| 7,239,769 B2 * | 7/2007 | Yang et al. | 385/16 |
| 7,309,621 B2 * | 12/2007 | Conley et al. | 438/99 |
| 7,498,824 B2 * | 3/2009 | Lane | 324/715 |

(Continued)

FOREIGN PATENT DOCUMENTS

| | | | |
|---|---|---|---|
| KR | 1020070099462 | 10/2007 | |
| KR | 100779090 | 11/2007 | |
| WO | WO 2008/010638 | * 1/2008 | G01N 27/12 |

OTHER PUBLICATIONS

Sensors and Actuators B. Chemical vol. 138.2 (Jinmyoung Jo et al.) May 6, 2009 "ZnO nanorod-coated quartz crystals as self-cleaning thiol sensors for natural gas fuel cells" see pp. 485-487; figs 1-2, Retrieved from: http://www.sciencedirect.com/science.

(Continued)

*Primary Examiner* — Richard Isla Rodas
(74) *Attorney, Agent, or Firm* — Finnegan, Henderson, Farabow, Garrett & Dunner LLP

(57) ABSTRACT

A sulfur concentration detection system for detecting a sulfur concentration in a liquid includes a sensor having a conductive metal substrate and zinc oxide microstructures deposited on and protruding from the conductive metal substrate, a current source, and a voltage detector. An electrical resistivity of the zinc oxide microstructures is configured to change as a function of an amount of sulfur in the liquid available to react with zinc in the zinc oxide microstructures. The current source and the voltage detector are connected to the conductive metal substrate and configured to detect a change in the electrical resistivity of the zinc oxide microstructures.

17 Claims, 4 Drawing Sheets

(56) References Cited

U.S. PATENT DOCUMENTS

| | | |
|---|---|---|
| 7,520,163 B2 | 4/2009 | Kinkade, Jr. et al. |
| 2003/0217922 A1* | 11/2003 | Suganuma et al. ........... 204/426 |
| 2007/0227910 A1 | 10/2007 | Sommer et al. |
| 2008/0006531 A1 | 1/2008 | Holt |
| 2008/0165361 A1 | 7/2008 | Kauffman |
| 2008/0257785 A1 | 10/2008 | Varma et al. |
| 2009/0286351 A1* | 11/2009 | Hirao et al. ................... 438/104 |
| 2011/0290003 A1* | 12/2011 | Liu et al. ...................... 73/31.06 |
| 2012/0174656 A1* | 7/2012 | Rebinsky et al. ............ 73/61.41 |
| 2012/0192626 A1* | 8/2012 | Rebinsky et al. ............ 73/61.41 |

OTHER PUBLICATIONS

Journal of Denistry vol. 35.7 (Naoko Tanda et al.) Dec. 31, 2007 "A new portable sulfide monitor with a zinc-oxide semiconductor sensor for daily use and field study" see pp. 552-557; fig 2, Retrieved from: http://www.sciencedirect.com/science.

* cited by examiner

ZINC OXIDE SULFUR SENSOR

TECHNICAL FIELD

The present invention relates generally to sulfur sensors. More particularly, the present invention relates to sulfur sensors that can be used to detect ultra low concentrations of sulfur in liquids, such as below even 15 ppm.

BACKGROUND

It is important to be able to accurately and reliably measure the concentration of sulfur in liquids, as various chemical reactions may take place that would release sulfur compounds into the atmosphere or onto physical structures around the sulfur-containing liquid. For example, the combustion of diesel fuel typically generates sulfur oxides ($SO_2$, $SO_3$) and sulfuric acid (condensate $H_2SO_4$), both of which are components of acid rain. Further, these sulfur compounds have been linked to catalyst poisoning in diesel particulate filters (DPFs) and sulfuric acid condensation and corrosion of engine components, such as the cooler and piston ring liner components. Such phenomena are found when using both high sulfur (>350 ppm) and low sulfur (10-350 ppm) fuels.

For various reasons, including the sensitivity of aftertreatment components to sulfur compounds, many modern diesel engines are now being designed to use Ultra Low Sulfur Diesel fuel (<15 ppm S). Accordingly, the sulfur level of the fuel source is of utmost importance for optimum machine performance. While sulfur detection in liquids at levels below 15 ppm is attainable in a laboratory or other test setting, such detection is not feasible in the field with an accurate, portable, reliable, quick, and inexpensive sensor. Examples of known means of detecting sulfur at ultra-low levels include Flame Photometry Detection (FPD) and Inductively Coupled Plasma (ICP) devices, but both are more appropriately used in the laboratory setting because of their size and duration of test cycles. Accordingly, a desire for a fast and inexpensive detection of sulfur level in diesel fuels, or possibly an on-board diagnostic tool for determining the same, persists.

SUMMARY OF THE INVENTION

In one aspect, the present disclosure is directed to a sensor for determining a sulfur concentration in a liquid. The sensor comprises a substrate that includes a conductive material. The sensor also includes zinc oxide microstructures protruding from the substrate.

In another aspect, the present disclosure is directed to a sulfur concentration detection system. The detection system comprises a sensor having a substrate including a conductive material and zinc oxide microstructures protruding from the substrate. The system includes a current source and a voltage detector, wherein the current source and voltage detector are connected to the substrate.

In yet another aspect, the present disclosure is directed to a method for determining the sulfur concentration in a liquid. The method comprises exposing the liquid to a sulfur sensor, where the sensor has a substrate including a conductive material and zinc oxide microstructures protruding from the substrate. The method then includes applying a constant current to the substrate, monitoring the voltage corresponding to the applied current, and measuring the amount of time required for the voltage to change by at least about 25%. After this, the method includes the step of correlating the time required for the voltage to change by at least about 25% to a concentration of sulfur in the liquid.

BRIEF DESCRIPTION OF THE DRAWINGS

Whenever possible, the same reference numbers will be used throughout the drawings to refer to the same or like parts.

DETAILED DESCRIPTION

Figure 1:
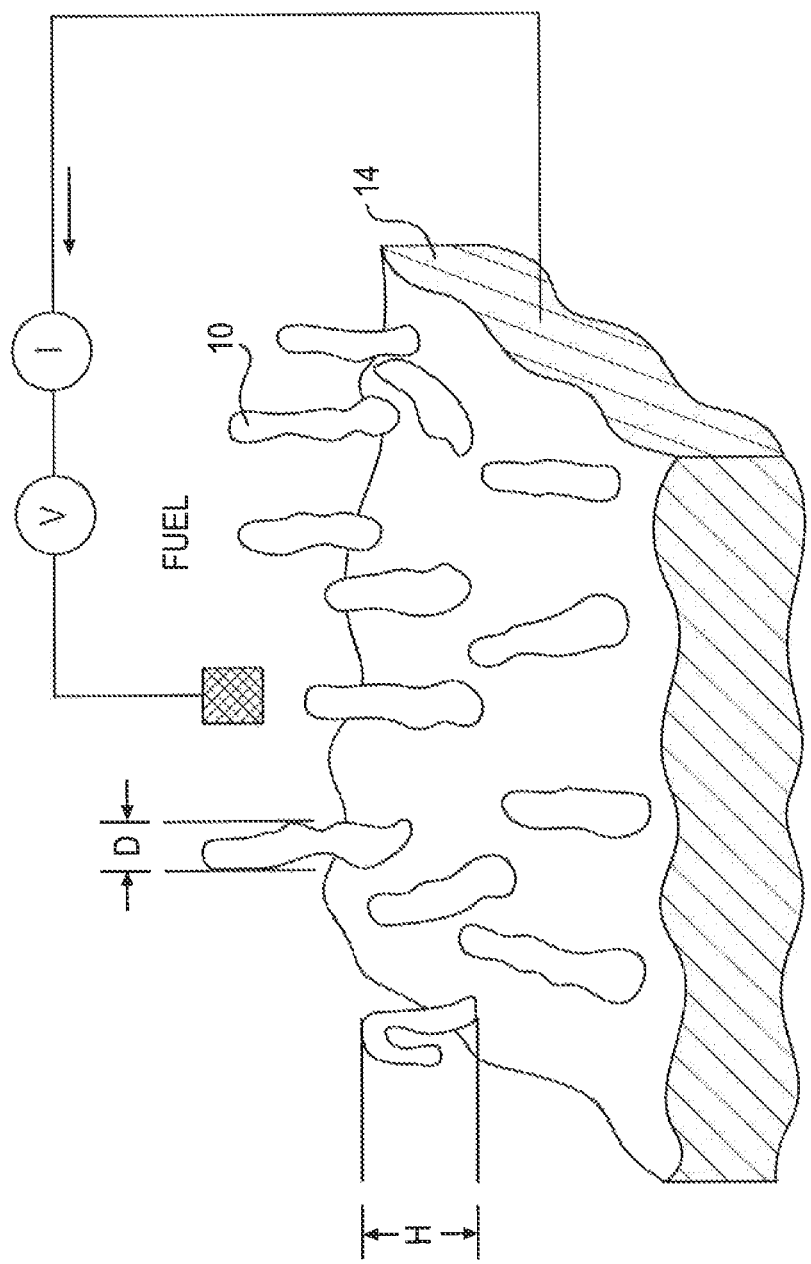
FIG. 1 is a cross-sectional illustration of zinc oxide microstructures on a conductive substrate as disclosed herein.

With reference to the drawings, FIG. 1 shows a cross-section of a zinc oxide (ZnO) sulfur sensor according to the disclosure. The sulfur sensor has ZnO microstructures 10 protruding from a substrate 14. While the term "microstructures" is used herein to describe the nature and size of the protrusions, one skilled in the art should understand that the actual scale of said protrusions may approach or enter the nano-scale or, alternatively, be larger than the micro-scale.

The sulfur sensor is designed based on the physical adsorption of organ-sulfur compounds onto ZnO. The rate of physical adsorption of organo-sulfur compounds onto ZnO is a function of surface area, which can be increased by controlling the shape of the protrusions when producing the coating. This physical adsorption is based, as least in part, on the good sorption affinity of ZnO with organo-sulfur compounds because of the crystal phase in the ZnO coating of microstructures. The physical adsorption of organo-sulfur compounds onto the ZnO protrusions results in a change in resistivity of the outer layer of the ZnO microstructures. The amount of changed material corresponds directly to the amount of sulfur in the liquid available to react with the zinc in ZnO microstructures 10, which can be measured by measuring the voltage change for a known current applied to the sulfur sensor.

Substrate 14 of the sulfur sensor is a conductive material capable of supporting ZnO microstructures and being used to carry a current for determining the voltage change in the microstructures. Exemplary materials include copper or a stainless steel, such as 316 stainless steel.

ZnO microstructures 10 may be formed on substrate 14 using any suitable deposition technique. ZnO microstructures 10 may take on a variety of shapes which are suitable for reaction with the sulfur in the liquid. One advantage to forming microstructures having a protruding orientation away from substrate 14 is the increased surface area available to interact with the sulfur compounds, which not only increases the amount of ZnO available for the physical adsorption, but also increases the sensitivity of the sulfur level measurement. ZnO microstructures 10 may, for example, take on the shape of micro-rods or micro-ribbons. Such forms can be readily achieved using Metal Organic Chemical Vapor Deposition (MOCVD), or any other suitable coating or deposition process known in the art.

As shown in FIG. 1, ZnO microstructures 10 protrude outward from conductive substrate 14, designated as the measurement H, by at least about 0.1 μm, such as between about 0.1 μm and about 1.0 cm, between about 0.1 μm and about 200

μm, or between about 0.1 μm and about 1.0 μm. Moreover, the width of the micro-ribbon or diameter of the micro-rod, shown as measurement D, is at least about 0.1 μm, such as between about 0.1 μm and about 3 μm, or between about 0.1 μm and about 1.5 μm, such as between about 0.1 μm and about 1.0 μm.

Figure 2:
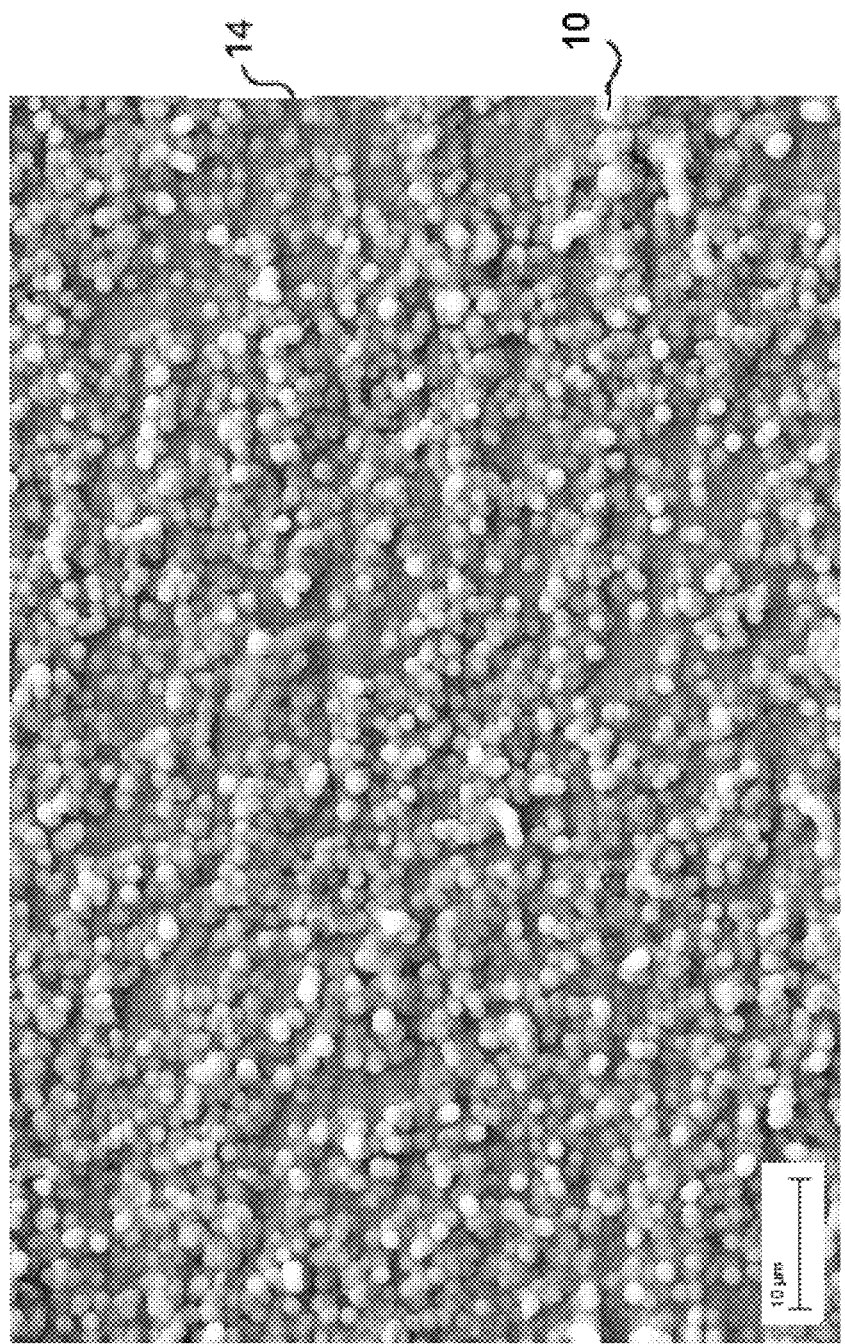
FIG. 2 is an SEM micrograph of the surface of a substrate coated with zinc oxide microstructures at approximately 5000×.

FIG. 2 shows an SEM micrograph of the surface of a ZnO sulfur sensor according to the disclosure. As can be seen in FIG. 2, the density of ZnO microstructures 10 is at least about 60% of the surface area of substrate 10. In most instances, however, complete coverage of substrate 10 is not desirable, as such dense coverage may inhibit ZnO interaction with sulfur in the liquid. Accordingly, the coverage of ZnO microstructures 10 on the surface of substrate 10 is between about 30%-99%. Moreover, it has been discovered that the density of the microstructures may be dependent on the composition of the substrate. For example, when the substrate is copper or another highly conductive substrate, the coverage of ZnO microstructures 10 may be lower, such as between about 30%-80%, or between about 30%-60%, or even between about 30%-40%. But for less conductive substrate materials, such as stainless steel, the coverage of ZnO microstructures 10 may be higher, such as between about 60%-99%, such as between about 75%-98%, or between about 85%-98%.

INDUSTRIAL APPLICABILITY

The sensor disclosed herein is particularly useful in field applications to allow operators to determine the sulfur content of a fuel before introducing the fuel into the machine. The sensor disclosed herein may be modified to be a disposable sensor, a reusable sensor, or an on-board sensor that determines the sulfur content of the fuel in the fuel tank neck before an appreciable amount of fuel is introduced.

Figure 3:
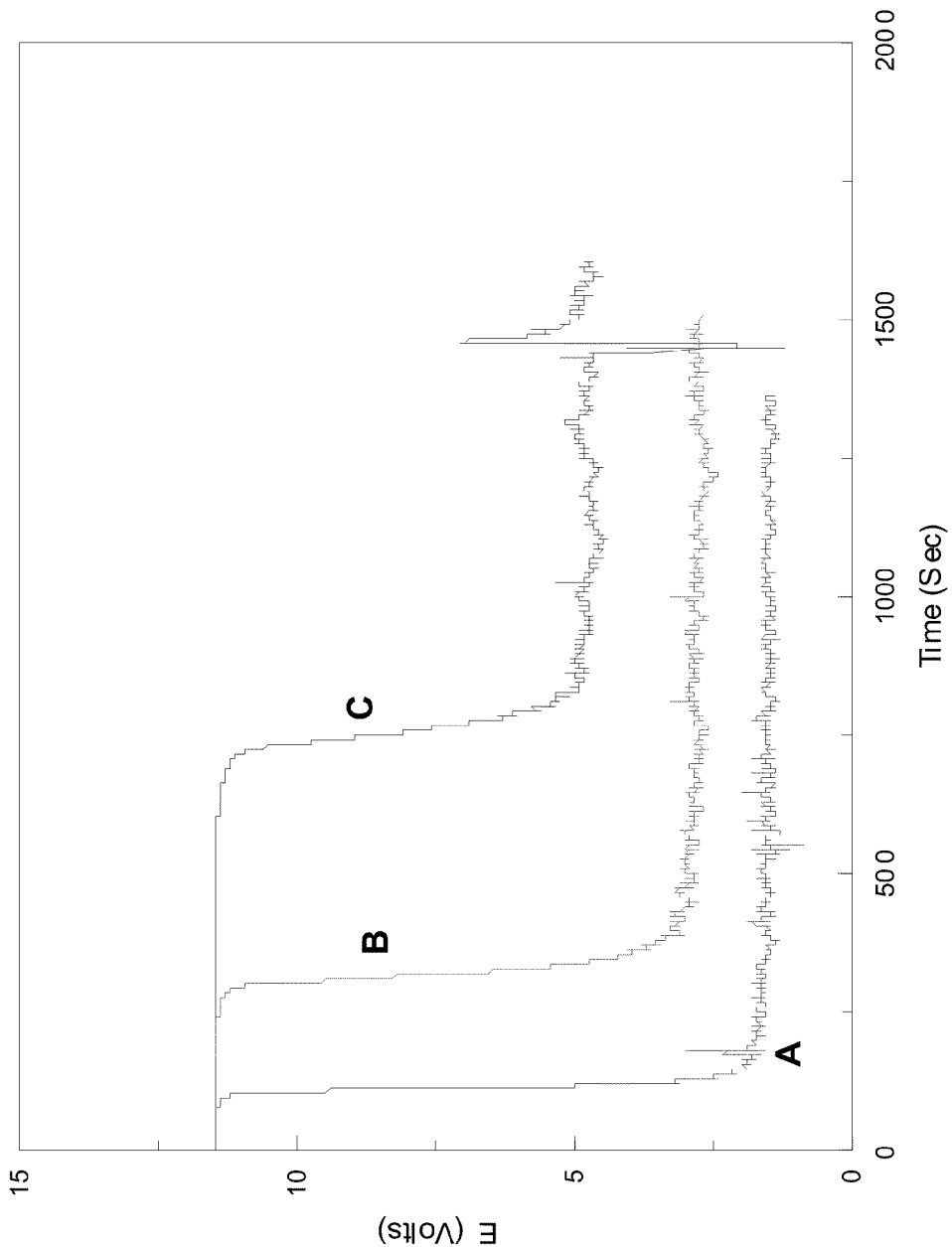
FIG. 3 is a chart showing the change in voltage over time for differing concentrations of sulfur in liquid using a sensor disclosed herein.

FIG. 3 shows the results of exposing a series of exemplary ZnO sulfur sensors formed according to the disclosure to a variety of liquids having various sulfur concentrations. Specifically, the ZnO microstructures were formed on copper substrates using MOCVD. The results show how the voltage applied across Sensor A at a constant current changed over time when the sensor was exposed to a liquid having 350 ppm sulfur. Sensor B was exposed to a liquid having 15 ppm sulfur, and Sensor C was exposed to a liquid having 1 ppm sulfur. As can be seen, Sensor A reached a saturation point at about 2 minutes, while Sensor B was saturated at about 5.8 minutes and Sensor C was saturated at about 12.5 minutes.

According to the results of the experiment that yielded the data for FIG. 3, an operator could monitor the amount of time necessary for saturation of a ZnO sulfur sensor, as indicated by a change in voltage across the sensor of at least about 25%, or at least about 35%, or even at least about 50%. The operator could then correlate the time necessary for saturation of the sensor to a sulfur content using a lookup table, or the correlation could be automated using known automating techniques, such as a computer accessing a series of lookup tables, and an absolute sulfur reading could be issued to the operator.

Figure 4B:
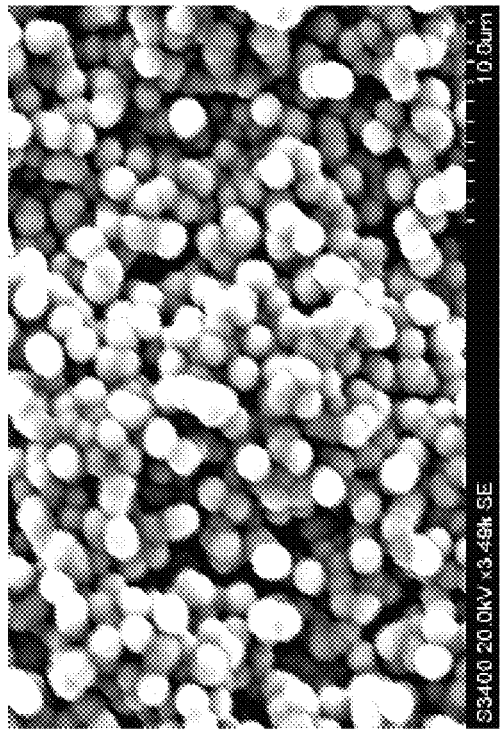
FIG. 4B is a photomicrograph of the surface of a substrate coated with ZnO microstructures as disclosed herein at about 3.5 hours of growth at about 1900×.
Figure 4A:
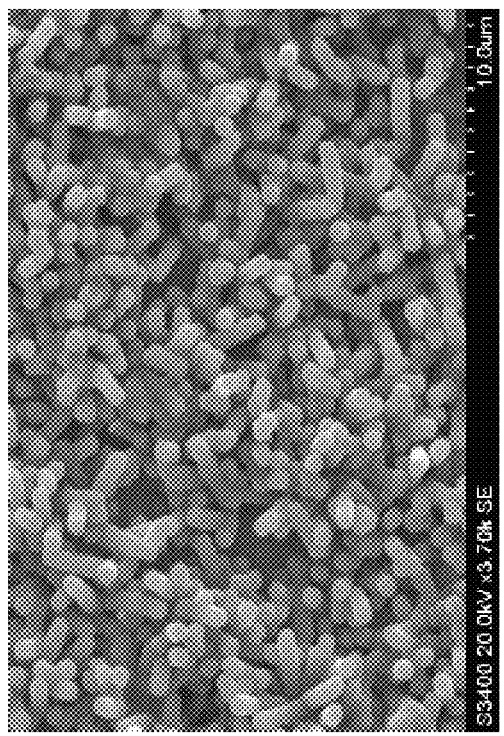
FIG. 4A is a photomicrograph of the surface of a substrate coated with ZnO microstructures as disclosed herein at about two hours of growth at about 1900×.

To form the ZnO microstructures on the conductive substrate, any suitable deposition and/or growth method known in the art may be used. For example, as noted above, MOCVD may be used to form ZnO deposits on the conductive substrate. FIGS. 4A and 4B show the affect of the time of the deposition process on the size and density of the ZnO microstructures on the conductive substrate. FIG. 4A shows ZnO microstructures that have been grown over about two hours, whereas FIG. 4B shows ZnO microstructures grown under the same conditions over about 3.5 hours. The thickness of the ZnO micro-structures shown in FIG. 4A is about 0.7 μm and the density is appropriate to allow the ZnO microstructures to grow in highly random directions away from the substrate. By comparison, the thickness of the ZnO microstructures shown in FIG. 4B is about 1.0 μm. While this thickness in itself is acceptable, the density of the ZnO on the surface of the conductive substrate is too high, nearing 100%, which inhibits interaction between the microstructures and the liquid. Such a high density is indicated in the photomicrograph from the end-on view of nearly all of the microstructures, which suggests that the density is so high, the ZnO microstructures are forces to grow in a highly compact, ordered fashion away from the substrate.

While the disclosure has referred to the microstructures as being ZnO microstructures, one skilled in the art should appreciate that the microstructures may have incidental amounts of other elements, likely drawn from the substrate during the deposition and growth process. For example, when the conductive substrate is a stainless steel, the microstructures may have between about 1.0-5.0 wt % C, between about 14.0-24.0 wt % O, between about 0.5-1.5 wt % Cr, and between about 2.5-7.0 wt % Fe, the balance being Zn. In one example, analysis showed that ZnO microstructures grown on a stainless steel substrate had the following composition, by weight percent:

C—3.31
O—17.90
Cr—1.04
Fe—4.53
Zn—73.22

Regarding the time necessary to accurately detect the sulfur content in the liquid, among other factors, this is highly dependent on the conductivity of the substrate, the total surface area of the ZnO microstructures exposed to the liquid, and the sulfur concentration of the liquid. In one example where ZnO microstructures were formed on a stainless steel substrate, the following data was collected for the corresponding sulfur concentration:

| Sample | Sulfur Level (ppm) | Response Time (s) | Potential (V) |
|---|---|---|---|
| 1 | 5 | 95 | 4.5 |
| 2 | 386 | 70 | 8.0 |
| 3 | 4940 | 50 | 15.5 |

As can be seen from this data, as sulfur level of the liquid increases, the response time decreases and the voltage increases when a ZnO sulfur sensor formed per this disclosure is used to test the sulfur level of fuel.

Although the present inventions have been described with reference to exemplary embodiments, workers skilled in the art will recognize that changes may be made in form and detail without departing from the sprit and scope of the invention. For example, although different exemplary embodiments may have been described as including one or more features providing one or more benefits, it is contemplated that the described features may be interchanged with one another or alternatively be combined with one another in the described exemplary embodiments or in other alternative embodiments. Because the technology of the present invention is relatively complex, not all changes in the technology are foreseeable. The present invention described with reference to the exemplary embodiments and set forth in the flowing claims is manifestly intended to be as broad as possible. For example, unless specifically otherwise noted, the claims reciting a single particular element also encompass a plurality of such particular elements.

What is claimed is:

1. A sulfur concentration detection system for detecting a sulfur concentration in a liquid, the detection system comprising:
- a sensor having a conductive metal substrate made of stainless steel or copper, and zinc oxide microstructures deposited on and protruding from the conductive metal substrate, an electrical resistivity of the zinc oxide microstructures being configured to change as a function of an amount of sulfur in the liquid available to react with zinc in the zinc oxide microstructures;
- a current source; and
- a voltage detector,
- wherein the current source and the voltage detector are connected to the conductive metal substrate and configured to detect a change in the electrical resistivity of the zinc oxide microstructures.

2. The sulfur concentration detection system of claim 1, wherein the zinc oxide microstructures have a rod-like form.

3. The sulfur concentration detection system of claim 1, wherein the zinc oxide microstructures cover between 30% to 99% of a surface area of the conductive metal substrate.

4. The sulfur concentration detection system of claim 1, wherein at least one microstructure of the zinc oxide microstructures is configured to expose an entire surface area of the at least one microstructure above the conductive metal substrate to the liquid, the liquid containing sulfur.

5. The sulfur concentration detection system of claim 1, wherein the zinc oxide microstructures have a width of at least 0.1 μm.

6. The sulfur concentration detection system of claim 1, wherein the zinc oxide microstructures have a width between 0.1 μm and 3 μm.

7. The sulfur concentration detection system of claim 1, wherein the zinc oxide microstructures protrude from the conductive metal substrate by a length of at least 0.1 μm.

8. The sulfur concentration detection system of claim 1, wherein the zinc oxide microstructures protrude from the conductive metal substrate by a length between 0.1 μm and 1.0 cm.

9. The sulfur concentration detection system of claim 1, wherein the conductive metal substrate has a width of at least about 2.0 mm.

10. The sulfur concentration detection system of claim 1, wherein the conductive metal substrate has a width between 2.0 mm and 30 mm.

11. The sulfur concentration detection system of claim 1, wherein the conductive metal substrate has a length of at least 2.0 mm.

12. The sulfur concentration detection system of claim 1, wherein the conductive metal substrate has a length between 2.0 mm and about 50 mm.

13. The sulfur concentration detection system of claim 1, wherein the zinc oxide microstructures cover between 30% to 80% of a surface area of the conductive metal substrate.

14. The sulfur concentration detection system of claim 1, wherein the zinc oxide microstructures cover between 60% to 99% of a surface area of the conductive metal substrate.

15. The sulfur concentration detection system of claim 1, wherein the zinc oxide microstructures have a ribbon-like form.

16. A method for determining a sulfur concentration in a liquid, the method comprising:
- exposing a sulfur sensor to the liquid, the sulfur sensor having a substrate comprising a conductive material and zinc oxide microstructures protruding from the substrate;
- applying a constant current to the substrate;
- monitoring a voltage corresponding to the constant current applied to the substrate;
- measuring an amount of time required for the voltage to change by at least 25%; and
- correlating the time required for the voltage to change by at least 25% to the sulfur concentration in the liquid.

17. The method of claim 16, wherein the liquid is a fuel.

* * * * *